United States Patent [19]
Bohlen et al.

[11] Patent Number: 4,675,383
[45] Date of Patent: Jun. 23, 1987

[54] PURIFICATION OF T-CELL GROWTH FACTOR

[75] Inventors: Peter Bohlen, San Diego; Gunther Dennert, South Pasadena, both of Calif.

[73] Assignee: The Salk Institute for Biological Studies, San Diego, Calif.

[21] Appl. No.: 670,285

[22] Filed: Nov. 9, 1984

Related U.S. Application Data

[63] Continuation-in-part of Ser. No. 551,963, Nov. 15, 1983, abandoned.

[51] Int. Cl.$^4$ ............................ C07K 3/20; C07K 3/28
[52] U.S. Cl. .................................... 530/351; 530/412; 530/417; 530/416; 435/68
[58] Field of Search ............. 260/112 R; 435/68, 948; 210/198.2, 927, 656

[56] References Cited

U.S. PATENT DOCUMENTS

| | | | |
|---|---|---|---|
| 4,289,690 | 9/1981 | Pestka et al. | 260/112 R |
| 4,377,482 | 3/1983 | Rivier | 260/112 R |
| 4,401,756 | 8/1983 | Gillis | 435/68 |
| 4,406,830 | 9/1983 | Fabricius et al. | 260/117 R |
| 4,490,289 | 12/1984 | Stern | 435/68 |

OTHER PUBLICATIONS

Gillis et al., Molecular Characterization of IL-2, *Immunol. Rev.* 63, pp. 167-209 (1982).
Robb et al., *Proc. Natl. Acad. Sci. USA.* 80, pp. 5990-5994 (1983).
Taniguchi et al., *Nature,* vol. 302, pp. 305-310 (1983).
Milestone et al., *Biochem. Biophy. Res. Comm.,* vol. 115, pp. 762-768 (1983).
Anzano et al., *Analytical Biochemistry* 125, pp. 217-224 (1982).
Fuhrer et al., *J. Chromato* 248(3), pp. 427-433 (1982).
FASEB 1982, *Lymphokine Res.,* vol. (2), pp. 51-57 (1982).
Ihle et al., *J. Immunol.* 129 (6), pp. 2431-2436 (1982).
Mahoney, *Biochem. Biophy. Acta.* 704, pp. 284-289 (1982).
Purification of Mouse IL-2 to Apparent Homogeneity, *JBC* 258(20) 1983, pp. 12114-12117, Riendeau et al.
A Rapid Large Scale Purification Procedure for Gibbon IL-2, *J. Immunol.* 131(2) 1983, pp. 810-815, Henderson.
Control of the Expression of IL-2 Activity *Cell Immunol.* 73, pp. 106-114 (1982) Henriksen et al.
HPLC and Its Application to Protein Chemistry *Advances Chromatography,* (NY) (1981) Chapter 1, pp. 1-84 Hearn.
High-Performance Liquid Chromatography of Proteins, *Analytical Biochemistry* 103, pp. 1-25 (1980) Regaier et al.
Quantitative Determination of Amino Acids ... HPLC, *Biochem. Biophys. Res. Comm.,* 108(2), pp. 783-790 (1982) Rabus et al.

*Primary Examiner*—Morton Foelak
*Assistant Examiner*—Garnette D. Draper
*Attorney, Agent, or Firm*—Fitch, Even, Tabin & Flannery

[57] ABSTRACT

Substantially homogenous T-cell growth factor is isolated. A multiple-step purification procedure of T-cell growth factor-containing biological sample includes at least one reverse-phase HPLC fractionation using a C3 to C5 silica gel stationary phase. A preferred pre-purification protocol includes concentration of the biological sample on a semipermeable medium followed by gel filtration and semi-preparative reverse-phase HPLC on a hydrophobic stationary phase. Fractionating the pre-purified biological sample with two or three reverse-phase HPLC fractionations using C3 to C5 silica gel stationary phase yields T-cells growth factor of over 90% purity.

19 Claims, No Drawings

PURIFICATION OF T-CELL GROWTH FACTOR

This invention was made with Government support under Grants Nos. AM-18811 and HD-09690, awarded by the National Institutes of Health. The Government has certain rights in this invention.

This application is a continuation-in-part of U.S. patent application Ser. No. 551,963 filed Nov. 15, 1983 now abandoned. The present invention relates to purification of a mammalian protein and more particularly to purification of T-cell growth factor or interleukin-2.

BACKGROUND OF THE INVENTION

T-cell growth factor (TCGF), also termed interleukin-2 (IL-2), has been previously described and has been recognized as an important member of the family of lymphokines which are lymphocyte-derived regulatory proteins that play a role in cellular and humoral immune responses. TCGF is released from antigen-, phorbolester-or lectin-stimulated cultured T-cells and causes proliferation of primed T-lymphocytes and natural killer (NK) cells. It facilitates the indefinite in vitro growth of functional T-cells and NK cells, and if injected into tumor-bearing animals, it may facilitate an elevated immune response to the tumor.

Because TCGF has been recognized for a number of years as an important protein with potential clinical use, there has been a substantial amount of research directed to characterizing its properties. Research in this respect has been hindered somewhat by the lack of a suitable procedure for obtaining meaningful quantities of truly pure TCGF. As a result, characterization of TCGF have often been at variance, undoubtedly due to the presence of contaminating proteins, the relative proportions of which depend upon the method of partial purification. Heretofore, there has been no generally useful method described which isolates a truly pure fraction of human TCGF in a quantity which permits its characterization, although analytical techniques, such as electrophoresis or isoelectric focusing, have been used to analyze impure protein fractions and may produce bands which contain minute amounts of pure TCGF.

Applicants herein have been studying TCGF since 1976, and for seven years had been somewhat frustrated in their research in their inability to obtain substantially pure human TCGF. Applicants attempted purifications based upon a variety of published techniques and also modified such published techniques in attempts to enhance the purity. In particular, applicants attempted to perform high performance liquid chromatography (HPLC) using available hydrophobic stationary phases, but without complete success. The highly hydrophobic stationary phases proved to have too great an affinity for TCGF, resulting in broadening of the elution peaks and inevitable overlap with peaks with those of contaminating proteins. Furthermore the high affinity of hydrophobic stationary phases for TCGF substantially reduced the percent recovery, that is, the total activity of TCGF in the eluted fractions as compared to the total activity of the TCGF in the material supplied to the HPLC column. Thus, there has been an existing need of applicants and other researchers for a process of isolating TCGF to substantial purity in a manner that is generally useful and also gives a high percentage recovery.

Several laboratories have reported partial purification of human TCGF from peripheral blood lymphocytes, Mier, J. W. et al., *J. Immunol.* 128, 1122–1127 (1982); Gillis, S., et al, *Immunol. Rev.* 63, 167–209 (1982); Robb, R. J. *Immunobiol.* 161, 21–50, (1982); from spleen leukocytes, Acuto, O., et al., *J. Immunol. Methods* 53, 15–26 (1982), and from the T-leukemia cell line, Jurkat, Gillis et al. supra; Robb, supra. However, in these literature reports, none of the compositions contains more than about 5 to 10 percent purity (as a weight percent of total protein).

Reindeau et al., *The Journal of Biological Chemistry* 258, 12114–12117 (1983) describe attempts to purify mouse interleukin-2. A C18 column was used in HPLC to purify IL-2 from EL4 cell secretions; however, as shown in FIG. 1, page 12115, there was no single elution peak, clearly evidencing that pure interleukin 2 was not obtained. Furthermore, recovery, even in this relatively impure condition, was only 70%. The paper also describes the synthesis of trace amounts of mouse IL-2 using mouse IL-2 messenger RNA to transcribe IL-2 in a cell-free wheat germ extract, followed by HPLC. Production of TCGF by messenger RNA transcription in this manner is not a practical method of producing useful amounts of TCGF.

Henricksen, O. and Frey, J., *Cellular Immunology* 73 106–114 (1982) describe a fractionation of mouse IL-2 which is characterized as a "partial purification" in the abstract of the article. The stationary phase is not clearly specified in the article, as the stationary phase is referred to only by a tradename that is inclusive of several stationary phases produced by the same manufacturer. The graphic representation of the HPLC elution in FIG. 3, page 112, clearly indicates that the partial purification produces a far from homogeneous IL-2 preparation.

Henderson et al., *The Journal of Immunology* 131, 810–815, (1983) describe a partial purification of gibbon TCGF using HPLC. Although the process provides a relatively good recovery of TCGF activity, no homogeneous TCGF fraction is obtained, as clearly evidenced by the graphic representation of the HPLC elution in FIG. 4, page 812.

Milstone, D. S., and Parker, C. W., *Biochemical and Biophysical Research Comm.* 115, 762–768, (1983) describe a purification of gibbon ape TCGF, including a HPLC fractionation on a C18 column. Although TCGF fractions are characterized as being in "highly purified form", it is clear from the elution graphs that homogeneous TCGF is not obtained. From a reading of the article in its entirety, it can be estimated that the gibbon TCGF obtained is at best about 50% pure. Furthermore, the recovery of TCGF as noted on page 766 is only about 50%, confirming applicants' own experience with hydrophobic columns and the problem of excessive affinity of TCGF for highly hydrophobic columns. The paper lacks an amino acid analysis that would establish the degree of purity and lacks any other reliable data that establishes purity. SDS-PAGE data, as set forth in this paper, is a relatively unreliable indicator of purity because proteins of similar molecular wt. run together.

Recently, Robb, et al., *Proc. Natl. Adac. Sci. USA* 80 5990–5994 (1983) have obtained highly purified TCGF from Jurkat cells in an immunoaffinity chromatography procedure that utilizes monoclonal antibodies specific to TCGF; however, this technique requires large amounts of antibodies and may be difficult to adapt to large-scale TCGF purification. Previous data has raised speculation as to whether TCGF from tonsil cell-derived peripheral blood lymphocytes (tTCGF) differs from Jurkat cell-derived TCGF (jTCGF). Recently, the structure of a cDNA for human Jurkat cell-derived TCGF has been established, Taniguchi, T., *Nature* 302 305–310 (1983).

Because TCGF has important value for promoting cell growth in vitro and may be important as a therapeutic agent in vivo, it would be desirable to have a method of obtaining sizable amounts of substantially pure TCGF. This is particularly the case where the substance is to be administered to a human or other mammal as administration of unseparated impurities is to be avoided whenever possible.

SUMMARY OF THE INVENTION

Conditioned media containing TCGF is obtained from both human tonsil cell culture and Jurkat cell culture, and TCGF is isolated from these media in a multiple-step purification procedure. The purification procedure consists of hollow-fiber concentration, gel filtration, semi-preparative reverse-phase high performance liquid chromatography (HPLC), and at least one and preferably at least two steps of analytical reverse-phase HPLC using relatively low hydrophobicity C3 to C5 silica gel as the stationary phase. Both jTCGF and tTCGF fractions of over 80–90 weight percent purity have been obtained. Substantially homogenous TCGF is useful for internal administration to mammals, particularly humans. Experiments with the substantially homogenous TCGF fractions indicate that jTCGF and tTCGF are either identical in structure or very nearly identical.

DETAILED DESCRIPTION OF THE PREFERRED EMBODIMENTS

In accordance with the present invention, TCGF (both tTCGF and jTCGF) is substantially purified by a multi-step procedure that includes concentration, e.g., using a semipermeable medium, gel filtration chromatography and several reverse-phase HPLC purifications. In particular, it is found that reverse-phase HPLC purifications in which the stationary phase has a low hydrophobicity, such as that provided by C3 to C5 silica gel, achieves a degree of purification, i.e., greater than about 80 weight percent. TCGF is a rather hydrophobic protein and is easily lost by adsorption onto hydrophobic surfaces due to hydrophobic interaction, and previous attempts at purifying TCGF have been hampered by such loss. Relatively low hydrophobicity reversed phases, such as C3 and C4 silica gel, are found to provide good recovery and high resolution of TCGF. Efficiency of the purification procedure is demonstrated by the fact that microgram amounts of TCGF can be isolated from relatively small quantities of conditioned medium.

It is desirable to start with a biological specimen having as high a titer of TCGF as possible. Lymphokine-producing cells secrete undetectable amounts of TCGF at all times; however, unless stimulated, they generally produce relatively low levels of lymphokines. Lymphokine-producing cells may, however, be stimulated to produce larger amounts of lymphokines by agents, such as phytohemagglutinin, lipopolysaccharides, phorbolesters, e.g., phorbol 12-myristate 13-acetate, and Concanavalin A (Con A), and it is preferred to so stimulate the cells and obtain the culture medium having relatively high levels of lymphokines from the stimulated cells.

To prepare the culture medium for gel filtration, it is necessary to substantially reduce its volume, preferably to about five percent or less of its original volume. Concentration may be carried out with a semipermeable material through which water molecules but not larger molecules, such as long chain proteins, pass. A preferred semipermeable material is a hollow-fiber semipermeable medium which has a large surface-to-volume ratio.

Initial separation of the components of the concentrated sample is achieved through gel filtration which separates large proteins according to their molecular weight. Gel filtration may be carried out, for example, on a column packed with Sephacryl. Fractions which are biologically active, exhibiting TCGF activity, are collected for further processing. To avoid having to perform bioassays on the fractions at each repetition of the purification procedure, it is acceptable to collect fractions containing proteins in the 14,000 to 17,000 molecular weight range. Eluent from the gel filtration procedure is estimated from bioassays performed on the eluent to contain between about 0.01 and about 0.1 weight percent TCGF, expressed as weight percent of the total protein in the eluent. The purification factor of gel filtration chromatography is relatively low, i.e., about 10-fold; however, it is a relatively simple procedure to perform and does remove substantial amounts of extraneous high molecular weight protein likely to interfere in subsequent HPLC steps.

While the gel filtration step removes significant amounts of extraneous protein, a relatively large volume of TCGF-containing eluent is obtained. This eluent is fractionated on a semi-preparative (or preparative) column which partially purifies the protein without requiring prior concentration of the gel filtration eluent. The semi-preparative (or preparative) HPLC fractionation is not considered the most critical step of the process but preferably should enhance the purity by a factor of about $10^3$ with substantially complete recovery. The partially purified TCGF fraction that is to be applied to the HPLC column should be at least about $10^2$ to $10^3$ TCGF units per mg. of protein, as determined by the bioassay system, hereinafter described in Example 1.

Stationary phases of a wide range of hydrophobicites may be used for the semi-preparative column, including silica gel columns ranging from about C3 to C18; however, lower C numbers, i.e., C8 or lower are preferred. The use of the stationary phase in the semi-preparative column is not as critical as in the final purifications because only a relatively rough purification is being performed, and relatively broad TCGF elution peaks are acceptable. Substantially complete recovery can be obtained from highly hydrophobic stationary phases in the semi-preparative fractionation by appropriate adjustment of the mobile phase and/or the time of elution. The mobile phase is preferably a gradient of an increasing concentration of a water-miscible organic solvent, such as acetonitrile or a short chain alcohol, e.g., ethanol, propanol or isopropanol, in water. Typically the concentration of the solvent increases from about 40 volume percent to about 60 volume percent with the remainder being substantially water. To promote TCGF stability, the pH of the mobile phase is adjusted to below about 5.

A very important factor in obtaining substantially homogenous TCGF is the use of a relatively low hydrophobicity stationary phase for reverse-phase HPLC and, in particular C3, C4 or C5 silica gel support, i.e., silica gel having 3, 4 or 5 carbon atom alkyl groups bound thereto. C3 and C4 columns are preferred. C3 to C5 silica gel supports are relatively new and are much less familiar to those who purify proteins than the longer carbon chain, more highly hydrophobic supports, such as C8 to C20 silica gel. As a starting point, a practitioner in the art is likely to use the hydrophobic supports with which they are most familiar. TCGF, however, is not well separated by the more hydrophobic supports, presumably because TCGF contains highly hydrophobic regions which attach too strongly to highly hydrophobic supports and elute only partially from such supports in broad bands without achieving a high degree of purity. It is found that with less hydrophobic supports, i.e., the C3 to C5 silica gel, TCGF elutes in surprisingly narrow bands and unexpectedly high purity.

There have been those who have suggested that the carbon chain length of the nonpolar stationary phase is relatively unimportant and that any improvement due to the use of short-chain alkyl-substituted supports is attributable to other factors, such as the degree of salanization of the matrix rather than the alkyl chain length, e.g., M. W. Hearn, "High Performance Liquid Chromatography and Its Application To Protein Chemistry", *Advances in Chromatography*, N.Y. (1982) at page 27. However, applicants have found that despite a great deal of experimentation with long-chain alkyl-substituted supports, the high affinity of TCGF for the support hinders good TCGF purification, whereas on the other hand, once C3–C5 supports were used substantially purified TCGF was surprisingly obtained.

A variety of mobile phase systems might be used with these supports, and the particular solid support depends in part on the mobile phase selected. Both volatile and non-volatile systems are useful as the mobile phase. The mobile phase should be either hydrophilic or weakly hydrophobic, in which case hydrophobic ion pairing is promoted.

Preferably the mobile phase is a gradient of an increasing concentration of a water-miscible organic solvent, such as acetonitrile or a short chain alkyl alcohol, e.g., ethanol, propanol or isopropanol, in water. Typically, during the HPLC fractionation, the organic solvent concentration in the mobile phase will be increased from about 40 percent by volume to about 60 percent by volume with the balance substantially water. The mobile phase is acidic, e.g., below about pH 5, to promote TCGF stability. TCGF separations on HPLC are generally carried out between about pH 2 and about pH 4, and preferably between about pH 2 and about pH 3. The pH is preferably adjusted with an organic acid, such as trifluoroacetic acid, but may also be adjusted with an inorganic acid, such as phosphoric acid. The pH may also be determined by an appropriate buffer system.

To obtain substantially homogeneous TCGF from a fraction that has been purified by gel filtration and semi-preparative fractionation, it is generally necessary to perform several analytical fractionations, typically at least two, preferably three, and in some cases even more. The number of analytical fractionations that are performed depends on the purity of the starting material and also the final degree of purity desired. It is found that two analytical fractionations on C3 to C5 columns generally yield TCGF of at least about 80 percent purity (as a weight percent of total protein) and three fractionations generally yield TCGF of at least about 90 weight percent purity.

Obtaining TCGF fractions of greater than 90 percent purity represents a very substantial improvement over previously described procedures. Unlike methods by which TCGF is purified by immunoaffinity chromatography or isoelectric focusing, this method is adapted to large scale purification. As a substantially homogenous substance, TCGF has utility which partially purified TCGF does not. In particular, homogenous TCGF may be administered internally, e.g., by injection, into a human as a pharmaceutical substance, whereas injection into a human of TCGF of less than 50 percent purity would not be indicated except in the most extreme circumstances. Although proteinaceous impurities in human TCGF fractions would not generally be expected to induce severe immune responses in other humans, there always exists the danger of deleterious side effects when unknown biological impurities are administered. Thus, it is believed that only substantially homogenous TCGF fractions have a chance of being approved by government regulatory agencies for internal administration to humans. In addition, further characterization of TCGF function is expected to be expedited considerably by the availability of substantially purified TCGF.

In addition to obtaining TCGF of very high purity, the use of C3 to C5 columns has provided excellent recovery of TCGF activity relative to the cell supernatant used as starting material. Generally between 80 and 100 percent of the TCGF activity of the supernatant is recovered as substantially pure TCGF using 2 or 3 HPLC fractionations on C3 to C5 columns.

The purification procedure of the present invention makes it possible to "farm" TCGF. Jurkat cells represent one line of immortalized cells which produce and secrete TCGF. It is expected that cell lines produced through recombinant DNA technology will secrete higher yields of TCGF, increasing the value of the purification procedure provided by the present invention. In particular, studies by others of the TCGF gene indicates that a TCGF precursor protein, which contains a signal peptide segment about twenty amino acid residues long, is likely to require relatively little processing and that therefore, the TCGF gene might be inserted into a rapidly proliferating prokaryotic cell, such as E-coli, and then the processing of the gene-encoded precursor might be performed in vitro. Alternatively, techniques are available for attenuating the TCGF gene so that it only encodes the TCGF peptide sequences and not the signal peptide segment, and if such an attenuated gene were found to express substantial amounts of product in a host cell, TCGF could be directly isolated from the culture medium.

Purification of the TCGF will now be described in greater detail by way of example.

EXAMPLE 1

Tonsils are obtained from a local hospital from patients undergoing tonsillectomy. Tissue is washed in ice cold saline, minced with scissors and meshed through a 30 mesh stainless steel screen. Cell debris is removed by filtration through nylon mesh. Cells are cultured in Falcon Tissue culture dishes at $2 \times 10^6$ cells per ml in RPMI 1640 supplemented with 2% fetal calf serum, $10^{-5}$M $\beta$-mercaptoethanol, 0.1 mM non-essential amino acids, 1 mM L-glutamine and 1 mM pyruvate. Lymphokine production is induced by addition of 10 $\mu$g/ml of phytohemagglutin (Gibco, Grand Island, N.Y.) and 10 ng/ml of phorbol 12-myristate 13-acetate (Sigma, St. Louis, Mo.) at the time of plating. Cell supernatant is harvested by centrifugation after 36–48 hrs. and filtered through a 0.45 μm Millipore membrane.

A batch of 2000 ml of conditioned medium is concentrated to a volume of 60 ml on a hollow fiber device (Amicon, Lexington, Mass.) Model CH-4, fiber cartridge no. H1P5-43) at 4° C.

Gel filtration of the 60 ml hollow fiber concentrate is performed using a Sephacryl S-200 (95×5 cm) column with a 10 mM Tris Cl, pH 7.5/0.5M NaCl elution buffer, and a flow rate of 66 ml/h, at 4° C. Fractions of 11 ml are collected, and aliquots of 10 μl or less used directly for bioassay.

Bioassay of TCGF is performed using the mouse cell line CTLL-2 (provided by M. Thoman, Scripps Clinic and Research Foundation). CTLL-2 cells are maintained in RPMI 1640 medium supplemented with 30% supernatant derived from Con A-stimulated rat splenocytes. Exponentially growing CTLL-2 cells are cultured for 24 hrs. in RPMI 1640 medium (without Con A supernatant) at a concentration of $10^5$ cells per ml. For assay purposes, cells are adjusted to a concentration of $6\times10^4$ cells per ml. 50 μl of cell suspension is mixed with 50 μl of test sample in complete RPMI 1640 medium, cultured in triplicate and pulsed on day 2 with 0.5 uCi $^3$H-thymidine per well for 5 hrs. Cells are collected with an automatic harvester and radioactivity is determined by liquid scintillation counting. One TCGF unit is defined as the amount causing half maximal incorporation of $^3$H-thymidine into DNA under the assay conditions described.

Semi-preparative reverse-phase HPLC on an Ultrasphere TM 25×1 cm, 5 cm particle size, 100 Å pore size C8 column (Altex, Berkeley, Calif.) is performed at room temperature using 1M pyridine acetate, with an n-propanol in water gradient (increasing from 40 volume percent to 60 volume percent) pH 4, as eluant at a flow rate of 0.8 ml/min. For loading, the pool of bioactive fractions (300 ml, corresponding to the 2000 ml of original condition medium) from the gel filtration is pumped directly through the column prior to starting the propanol gradient for TCGF elution. 3.2 ml. fractions are collected. Aliquots of 16 ul of each fraction are added to 100 μg human serum albumin (1 mg/ml), dried in a Speed-Vac (Savant, Hicksville, N.Y.) vacuum centrifuge and subjected to bioassay.

The initial analytical reverse-phase HPLC is performed on a RPSC, 7.5×46 cm. 5 μm particle size 300 Å pore size C3 column (Altex) using a 0.1% by volume trifluoroacetic acid, acetonitrile gradient (the concentration of acetonitrile increasing from 40 volume percent to 60 volume percent) in water as the mobile phase, a 0.6 ml/min flow rate and a 1.8 ml. fraction size. The pool of active fractions from 2 semi-preparative reverse-phase chromatographies, corresponding to 4000 ml of original conditioned medium, is diluted 3-fold with 0.2M acetic acid and loaded in the manner described above with respect to the semi-preparative fractionation, TCGF of 10 percent purity is obtained.

Further analytical reverse-phase HPLC is performed on a Vydac C4, 25×4.6 cm, 5 μm particle size, 300 Å pore size column (Altex). The sample corresponding to 4000 ml of original conditioned medium is eluted with the same mobile phase, and under the conditions described above for the initial analytical fractionation, TCGF of 50 percent purity is obtained. A second passage of the TCGF through a C4 column under identical conditions yields TCGF of about 90 percent purity.

EXAMPLE 2

The human T-leukemia cell line Jurkat, provided by Dr. A. Altman (Scripps Clinic and Research Foundation, La Jolla, Calif.) is cloned several times by limiting dilution in microtiter wells, and a high producer clone (Jurkat E4) is isolated and expanded in RPMI 1640 containing 10% fetal calf serum. For induction of TCGF, $10^6$ cells per ml are cultured in the medium used for induction of tonsil lymphocytes except that serum is omitted. Conditioned medium is collected by centrifugation and filtered through a 0.45 um membrane.

TCGF from conditioned medium of Jurkat T-leukemia cells is isolated using the same procedure described above in Example 1 for purifying the conditioned medium of tonsil cells with essentially the same results. The only notable observed difference is the presence of significantly less total protein in the bioactive fractions after gel filtration, which may be attributed to the fact that conditioned medium from Jurkat cells is prepared under serum free conditions. jTCGF of between 95 and 100 percent purity is obtained after the semi-preparative fractionation, a C3 fractionation and a single C4 fractionation.

Preliminary chemical characterization of the isolated TCGFs suggests that the structures of tonsil-derived and Jurkat-derived TCGF are identical or at least very closely related and in all likelihood correspond to the amino acid sequence predicted from the cDNA coding for Jurkat TCGF. This conclusion is drawn from several lines of evidence: (1) amino acid compositions are very similar; (2) experimentally established N-terminal sequence and molecular weight of tTCGF agree with those of jTCGF as expected from the cDNA sequence; (3) both factors are indistinguishable in their elution behavior in a highly resolutive chromatography; and (4) the in vitro biological activity of the TCGFs is virtually identical. In view of the high resolution power of reverse-phase HPLC for even very closely related peptides, one might expect the separation of TCGFs with varying carbohydrate content. In fact, experiments with Con A affinity chromatography as well as those by Mier and Gallo, (Mier, et al., supra.) who used several types of lectins failed to detect protein-bound carbohydrate in TCGF. In this context it is interesting to note that the cDNA-derived sequence of jTCGF lacks any N-glycosylation site.

The potential applications of TCGF in experimental biology and clinical medicine are plentiful. The availability of pure TCGF will lead to the production of specific antibodies suitable for the development of radioimmunoassays for experimental purposes and for the diagnosis of diseases of the immune system. Various types of T-cells and NK cells may be propagated and cloned in vitro which should be important for the understanding of the precise biological functions of these cells. Human TCGF is expected to have therapeutic potential for patients whose cellular and humoral immune system is impaired. For example, patients with a low blood count of certain T-lymphocytes or NK cells (as observed, e.g., after cancer chemotherapy, immunosuppressive therapy or radiation therapy) can be transfused with their own lymphocytes, which previously were propagated with TCGF in vitro, a procedure that has already been used in laboratory animals, Dennert, G., et al., *Nature* 300, 31–34 (1982). The modification of this method would be to culture a patient's lymphocytes in the presence of TCGF prior to such therapy.

For internal administration, purified TCGF will be admixed with a pharmaceutically acceptable diluent.

While the invention has been described in terms of certain preferred embodiments, modifications obvious to one with ordinary skill in the art may be made without departing from the scope of the invention. While the novel use of C3 to C5 silica gel reverse-phase HPLC for purification of TCGF is considered to be particularly important for achieving the unprecedented purity of TCGF, i.e., greater than about 90% representing a 170,000 fold increase from conditioned medium, it is expected that other procedures may be substituted for the pre-purification steps described with respect to the preferred embodiment. It is expected that ion exchange chromatography, e.g., on Mono-Q or mono-S columns (Pharmacia, Sweden), or chromatofocusing, e.g., on mono-P columns (Pharmacia), may be successfully used for pre-purification of TCGF. Any substitute pre-purification protocol should yield TCGF of at least about 0.1 percent purity (as a weight percent of total protein) and preferably at least about 1.0 percent purity.

Various features of the invention are set forth in the following claims.

What is claimed is:

1. A method of obtaining human T-cell growth factor purified to at least about 80% by weight of total protein comprising obtaining a biological sample containing significant levels of human TCGF, pre-purifying said biological sample, and purifying said pre-purified biological sample with at least two reverse-phase HPLC chromatographic fractionations each using a C3 to C5 silica gel stationary phase.

2. A method according to claim 1 wherein said pre-purification increases the purity of TCGF in said biological sample to at least five percent as expressed as a weight percent of total protein.

3. A method according to claim 1 wherein said pre-purification comprises concentrating said biological sample to substantially reduce its volume, gel filtrating said concentrated biological sample and collecting biologically active fractions therefrom, and fractionating said biologically active fractions with semi-preparative chromatography.

4. A method according to claim 3 wherein said semi-preparative fractionation step is a reverse-phase HPLC chromatography.

5. A method according to claim 3 wherein said biological sample is concentrated with a semipermeable medium.

6. A method according to claim 5 wherein said biological sample is concentrated with a hollow fiber semipermeable medium.

7. A method according to claim 3 wherein said concentrating step reduces the volume of said biological sample to at least about 5% of its initial volume.

8. A method according to claim 1 wherein at least three reverse-phase HPLC fractionations are performed with said C3 to C5 silica gel as the stationary phase.

9. A method according to claim 1 wherein said biological sample is the culture medium of a TCGF-producing cell line subjected to a lymphokine-inducing agent.

10. A method according to claim 1 wherein said biological sample is purified on reverse-phase HPLC using an aqueous mobile phase having a pH of below about 5 and an increasing concentration of a water-miscible organic solvent.

11. A method according to claim 1 wherein C3 to C4 silica gel is the stationary phase for each of said two fractionations.

12. A method of obtaining human T-cell growth factor (TCGF) purified to at least about 80% by weight of total protein comprising obtaining a biological sample containing human TCGF, pre-purifying said biological sample to at least five percent as expressed as a weight percent of total protein, and purifying said pre-purified biological sample with at least two reverse-phase HPLC chromatography fractionations each using a C3 to C5 silica gel stationary phase.

13. A method according to claim 12 wherein said pre-purification comprises concentrating said biological sample to substantially reduce its volume, gel filtrating said concentrated biological sample and collecting biologically active fractions therefrom, and fractionating said biologically active fractions with semi-preparative chromatography.

14. A method according to claim 13 wherein said semi-preparative chromatography uses a C3-C8 silica gel stationary phase, said first reverse-phase HPLC chromatography uses a C3 silica gel stationary phase and said second reverse-phase HPLC chromatography uses a C4 silica gel stationary phase.

15. A method according to claim 12 wherein said biological sample is obtained from a cultured cell line of lymphocyte derivation.

16. A method of obtaining a human T-cell growth factor (TCGF) purified to at least about 80% by weight of total protein comprising obtaining culture medium of a TCGF-producing cell line subjected to lymphokine-inducing agent; concentrating said culture medium to reduce its volume to at least about 5% of its initial volume; gel filtrating said concentrated culture medium, fractionating said biologically active fractions with semi-preparative reverse-phase HPLC chromatography conducted on a hydrophobic stationary phase, and collecting biologically active fractions therefrom to increase the TCGF concentration to at least five percent as expressed as a weight percent of total protein; and then purifying said pre-purified biological sample with at least two reverse-phase HPLC chromatography fractionations each using a C3 to C5 silica gel stationary phase.

17. A method according to claim 16 wherein said semi-preparative chromatography uses a C3-C8 silica gel stationary phase, said first reverse-phase HPLC chromatography uses a C3 silica gel stationary phase and said second and third reverse-phase HPLC chromatographies use C4 silica gel stationary phases.

18. A method according to claim 16 wherein said biological sample is obtained from a cultured cell line of tonsil origin.

19. A method according to claim 16 wherein said biological sample is concentrated with a hollow fiber semipermeable medium.

* * * * *